(12) United States Patent
Cawse

(10) Patent No.: US 8,981,033 B2
(45) Date of Patent: Mar. 17, 2015

(54) RESIN CURING AGENTS

(75) Inventor: John Cawse, West Wratting (GB)

(73) Assignee: Hexcel Composites Limited, Cambridge (GB)

( * ) Notice: Subject to any disclaimer, the term of this patent is extended or adjusted under 35 U.S.C. 154(b) by 189 days.

(21) Appl. No.: 13/520,342

(22) PCT Filed: Jan. 6, 2011

(86) PCT No.: PCT/GB2011/050011
§ 371 (c)(1),
(2), (4) Date: Jul. 3, 2012

(87) PCT Pub. No.: WO2011/083329
PCT Pub. Date: Jul. 14, 2011

(65) Prior Publication Data
US 2013/0217803 A1    Aug. 22, 2013

(30) Foreign Application Priority Data

Jan. 7, 2010    (GB) .................................. 1000182.4
Mar. 22, 2010    (GB) .................................. 1004722.3

(51) Int. Cl.

| | | |
|---|---|---|
| C08G 59/10 | (2006.01) |
| C08G 59/50 | (2006.01) |
| C08L 63/00 | (2006.01) |
| C07C 229/60 | (2006.01) |
| C07C 237/34 | (2006.01) |
| C07D 303/30 | (2006.01) |
| C07D 303/36 | (2006.01) |
| C08K 5/20 | (2006.01) |

(52) U.S. Cl.
CPC .............. C08L 63/00 (2013.01); C07C 229/60 (2013.01); C07C 237/34 (2013.01); C07D 303/30 (2013.01); C07D 303/36 (2013.01); C08G 59/504 (2013.01); C07C 2101/14 (2013.01); C08K 5/20 (2013.01)
USPC .......................................... 528/124; 528/123

(58) Field of Classification Search
None
See application file for complete search history.

(56) References Cited

U.S. PATENT DOCUMENTS

| | | | | |
|---|---|---|---|---|
| 3,932,360 | A | * | 1/1976 | Cerankowski et al. .......... 528/64 |
| 4,636,535 | A | * | 1/1987 | Wang et al. .................... 523/204 |
| 4,645,803 | A | * | 2/1987 | Kohli et al. .................... 525/423 |
| 4,746,718 | A | * | 5/1988 | Gardner et al. .................. 528/98 |
| 4,921,928 | A | * | 5/1990 | Tanino et al. .................. 528/111 |
| 4,975,471 | A | * | 12/1990 | Hayase et al. ................... 522/13 |
| 5,268,442 | A | | 12/1993 | Bradshaw et al. |
| 2009/0124690 | A1 | | 5/2009 | Alberte et al. |

FOREIGN PATENT DOCUMENTS

| | | | |
|---|---|---|---|
| DE | 1962602 A | | 6/1974 |
| EP | 0454983 A1 | | 11/1991 |
| EP | 1454963 A1 | | 9/2004 |
| GB | 1141206 A | | 1/1969 |
| GB | 1141206 A | * | 1/1969 |
| GB | 1182377 A | * | 2/1970 |
| GB | 2460050 A | | 11/2009 |
| JP | 60-195122 A | * | 10/1985 |
| JP | 60195122 A | | 10/1985 |
| JP | 61-126126 A | * | 6/1986 |
| JP | 61126126 A | | 6/1986 |

OTHER PUBLICATIONS

Acta Poloniae Pharmaceutica, 2005, vol. 62(6), Bartulewicz et al., pp. 451-455.
European Journal of Medicinal Chemistry, 2001, vol. 36(9), Chacon-Garcia et al., pp. 7321-7736.
Aurora Screening Library catalogue, 2009, CHEMCATS Acc. No. 2069733245. Compound with CAS Registry No. 618392-33-9.

* cited by examiner

*Primary Examiner* — Robert Sellers
(74) *Attorney, Agent, or Firm* — W. Mark Bielawski; David J. Oldenkamp

(57) ABSTRACT

A curable resin comprising a curing agent, wherein the curing agent comprises an adjustable structural unit having a stable chain-like arrangement which is adjustable to a stable ring-like arrangement, wherein the ring-like arrangement comprises the constituents of the chain-like arrangement with two terminal constituents exhibiting an attractive chemical interaction, and is adjustable back from the ring-like arrangement to the chain-like arrangement by separation of the two terminal constituents.

2 Claims, 2 Drawing Sheets

RESIN CURING AGENTS

TECHNICAL FIELD

The present invention relates to novel resin and curing agents capable of providing cured resins with both good toughness and high glass transition temperature.

BACKGROUND

Curable resin systems are widely known and have a wide range of uses in a variety of technical fields. These systems function by reaction between resin molecules and curing agents. Upon activation, e.g. by mixing together or by heating, functional groups on the curing agent react with functional groups on the resin molecule to form an extended polymeric network, which is the process known as curing.

The resulting cured resin has physical properties which are largely or entirely dictated by the choice of resin, the choice of curing agent and the curing regime employed. A wide variety of physical properties can be obtained by altering one or more of these variables.

A particularly useful physical property is for the cured resin to be mechanically tough and able to withstand an impact without brittle fracture. Such resins are particularly useful when involved in the manufacture of a structure.

However, it is known that cured resins which are tough generally tend to have a low glass transition temperature, which can make them unsuitable for use in structures. Known methods of increasing the glass transition temperature, generally involve the material becoming more brittle, which is again not appropriate for use in structures. Additionally, known methods of toughening a brittle resin commonly also reduce the glass transition temperature.

It would therefore appear that cured resin systems which are both mechanically tough and yet have a high glass transition temperature, so that they can be used in structural applications, are not readily achievable with known systems.

SUMMARY OF THE INVENTION

In a first aspect, the invention relates to a curable resin comprising a curing agent wherein the curing agent comprises an adjustable structural unit having a stable chain-like arrangement which is adjustable to a stable ring-like arrangement, wherein the ring-like arrangement comprises the constituents of the chain-like arrangement with at least two terminal constituents exhibiting an attractive chemical interaction, and is adjustable back from the ring-like arrangement to the chain-like arrangement by separation of the two terminal constituents.

Cured resins comprising such an adjustable structural unit can be made which have good toughness and high glass transition temperatures.

This is believed to be achieved by the adjustable unit providing a rigid and solid-like cured environment because each of its forms, chain-like and ring-like, are stable, thus providing a high glass transition temperature. However, when the cured resin is sufficiently stressed e.g. by tensile, shear, impact or flexure modes, the adjustable unit is able to adjust itself from one form or another (e.g. depending on whether the local environment is under compression or tension) allowing the cured resin to respond without fracture, which exhibits itself as greater toughness and possibly yield behaviour of the cured resin.

Typically the adjustable structural unit forms an integral component of the backbone of the curing agent. As the backbone is more likely to bear the stresses of local compression or tension, this enables the adjustable unit to adjust itself under local stress conditions to provide the above benefit.

It is important that the attractive chemical interaction is weaker than a covalent bond, so that it is the first to rupture when the curable resin or curing agent is stressed. The attractive chemical interaction may take a variety of forms, and can be, but is not limited to a hydrogen bond, an internal salt, a betaine, a charge transfer interaction, an electrostatic interaction or other non-covalent interaction capable of lending stability to the ring-like arrangement.

Preferably the attractive chemical interaction is a hydrogen bond. Such a bond involves a hydrogen atom bonded to an electronegative atom such as nitrogen, oxygen or fluorine, wherein the hydrogen then forms a hydrogen bond with a nearby nitrogen, oxygen or fluorine atom.

In order for the adjustable unit to form a hydrogen bond in its ring-like arrangement, preferably the adjustable structural unit comprises an available hydrogen bonded to a nitrogen, oxygen or fluorine and an available nitrogen, oxygen or fluorine constituent, the available hydrogen and available nitrogen, oxygen or fluorine being separated by from 3 to 10 atomic constituents. Thus, a ring-like arrangement having from 5 to 12 atomic constituents can be formed by formation of a hydrogen bond between the available hydrogen and the available nitrogen, oxygen or fluorine.

In a preferred embodiment the available nitrogen, oxygen or fluorine is oxygen. The available oxygen is typically bonded to one or two carbon atomic units, but preferably is double bonded to a single carbon atomic unit. When double bonded to a carbon the oxygen will not be a constituent of the backbone.

In a preferred embodiment the available hydrogen is bonded to a nitrogen atomic unit. Clearly the hydrogen will not be a constituent of the backbone.

Suitable examples of structural groups which may be a component of the adjustable structural unit include —CO—NH—, —CO—O—, —CHOH—, —CH$_2$NH—, —CHSH—. A particularly useful group is —CO—, and more particularly —CO—NH— and —CO—O—.

A particularly preferred embodiment involves the adjustable structural unit comprising a —CO— unit and an —NH— unit, wherein the C and N are separated by a chain of from 1 to 8 atomic constituents.

In view of the above, the strength of the attractive chemical interaction must be sufficient to provide stability to the ring-like arrangement but not so strong that it does not rupture when stressed. Thus, preferably the attractive chemical interaction has a strength of from 1 to 200 kJmol$^{-1}$, more preferably from 2 to 50 kJmol$^{-1}$ and most preferably from 5 to 30 kJmol$^{-1}$.

The ring-like arrangement may be well-defined and having an attractive chemical interaction between two clearly identifiable interacting species. However the ring-like structure may be stabilised by more than one identifiable interaction and in this case each such interaction may have a strength as described above.

In a cured resin environment the curable resin and curing agent molecules are quite close to each other and can therefore hinder the movement of the adjustable unit from one arrangement to another. It has therefore been found to be advantageous if the curing agent can form more than one ring-like arrangement each from a corresponding chain-like arrangement. For example, embodiments which can form two ring-like arrangements from two different chain-like arrangements are preferred.

It may be that some of the constituents of the curing agent belong to more than one chain-like structure and can thus belong to more than one ring-like structure. In this situation the curing agent can typically only form one such ring-like arrangement at any one time. In other words, there may be two adjustable units but only one can be in ring-like arrangement at any one time. However this is still advantageous, as the ability to form one of two available ring-like arrangements means the molecule has a statistically better chance of one ring-like arrangement not being hindered by neighbouring molecules.

As the curing agent adjusts from its chain-like structure to its ring-like structure, the molecule undergoes a significant shortening of its length. For example, if the functional reactive groups include a nitrogen, then the distance between two nitrogens can increase by from 5 to 150%, preferably from 20 to 120%, as the curing agent or curable resin moves from its ring-like arrangement to its chain-like arrangement.

The invention applies equally to a wide range of resin and curing agents. Suitable curable resins include epoxy, benzoxazine, polyester, polyurethane, polyurea, bismaleimide, cyanate ester, polyimide, azomethine, vinyl ester and polycarbonate.

The curing agent can have a wide variety of functional reactive groups for reacting with a suitable curable resin functional group. Examples of suitable curing agent functional groups include amine, isocyanate, cyanate, epoxide, acyl halide, carboxylic acid, hydroxyl, thiol, aldehyde, nitrile, chlorosulfonyl, ketene.

Epoxy resin curing systems are preferred and thus the curing agent preferably has an amine functional group.

The curing agents typically can be represented by

X1-B—X2 wherein X1 and X2 each comprise at least one functional reactive group, as discussed above, which may be attached to a rigid non-functional ring-like unit, for example an aromatic cycloaliphatic or heterocyclic group. Examples are benzene, naphthalene, anthracene, cyclohexane, pyridine, furan, thiophene, preferably benzene. The ring-like unit may in turn have additional non-reactive functionalities including alkyl, halogen, ester, and ether. The B sequence is bonded to the ring-like unit in each of X1 and X2.

The functional reactive groups on the X1 and X2 groups may be ortho, meta or para to the B-sequence. The meta and para positions are more preferred, with the most preferable being meta.

In a preferred embodiment, the curing agent is of the form X1-B—X2, wherein each of X1 and X2 is a benzene ring with an —$NH_2$ functional reactive group meta or para to the B-sequence The B-sequence comprises the adjustable structural unit and may take a wide variety of forms. It comprises a backbone, which is a chain of atomic constituents linking X1 to X2. Some or all of the adjustable unit is present in the backbone. The backbone may vary in length to a certain degree and suitably it comprises a chain of from 4 to 12 atomic constituents, preferably from 5 to 10 atomic constituents.

Typically the atomic constituents of the B-sequence are selected from the atomic constituents consisting of carbon, oxygen, sulphur, nitrogen, phosphorus and fluorine. In a preferred embodiment, the B-sequence comprises at least two —CO— groups.

A B-sequence comprising two —CO—NH— groups separated by from 1 to 8 atomic constituents is preferred, most preferably from 2 to 5 atomic constituents.

A B-sequence comprising two —CO—O— groups, separated by from 1 to 8 atomic constituents is also preferred, most preferably from 2 to 5 atomic constituents.

It has also been found to be highly beneficial for the B-sequence to comprise a cycloaliphatic group, particularly cyclohexane. Such a group can stabilise the ring-like arrangement because of the restricted nature of the conformational states of the cycloaliphatic group. As such, it is typically located between the two terminal constituents which exhibit an attractive chemical interaction.

It is particularly advantageous if the backbone includes two adjacent carbons in the cycloaliphatic group. In other words, the remainder of the backbone and B-sequence, are bonded to two adjacent carbons on the cycloaliphatic group. In this arrangement, the remainder of the backbone and B-sequence are preferably bonded to the cycloaliphatic group at carbons both in equatorial positions or both in axial positions.

The curing agents are particularly useful for structural applications. In such applications it is advantageous for the materials to have a moderately high melting point. Thus, in a preferred embodiment, the curing agents have a melting point of from 130° C. to 260° C., more preferably from 150° C. to 240° C.

As the materials are useful in structural applications, they are particularly suitable as a component of a prepreg. A prepreg comprises a fibre structure pre-impregnated with curable resin and curing agent, among other materials. Typically a number of plies of such prepregs are "laid-up" as desired and the resulting laminate is cured to produce a cured composite laminate.

Thus, the invention also relates to a prepreg comprising structural fibres and a curable resin comprising a curing agent as described herein.

Curing may be carried out in any suitable method known in the art, typically by exposure to elevated temperatures and optionally elevated pressure.

However, the curing agents may be liquid at or near room temperature, which is particularly useful for resin transfer moulding applications.

The resulting cured resin preferably has a glass transition temperature of greater than 100° C., preferably greater than 120° C., more preferably greater than 140° C.

The invention will now be illustrated with reference to the following examples and with reference to the following figures, in which FIG. 1 is an image of a curing agent according to the invention in ring-like arrangement FIG. 2 is an image of the curing agent shown in FIG. 1 in chain-like arrangement FIG. 3 is an image of another curing agent according to the invention in a first ring-like form with a cyclohexane group in its chain form.

EXAMPLES

A variety of epoxy curing agents according to the invention were prepared and are shown below.

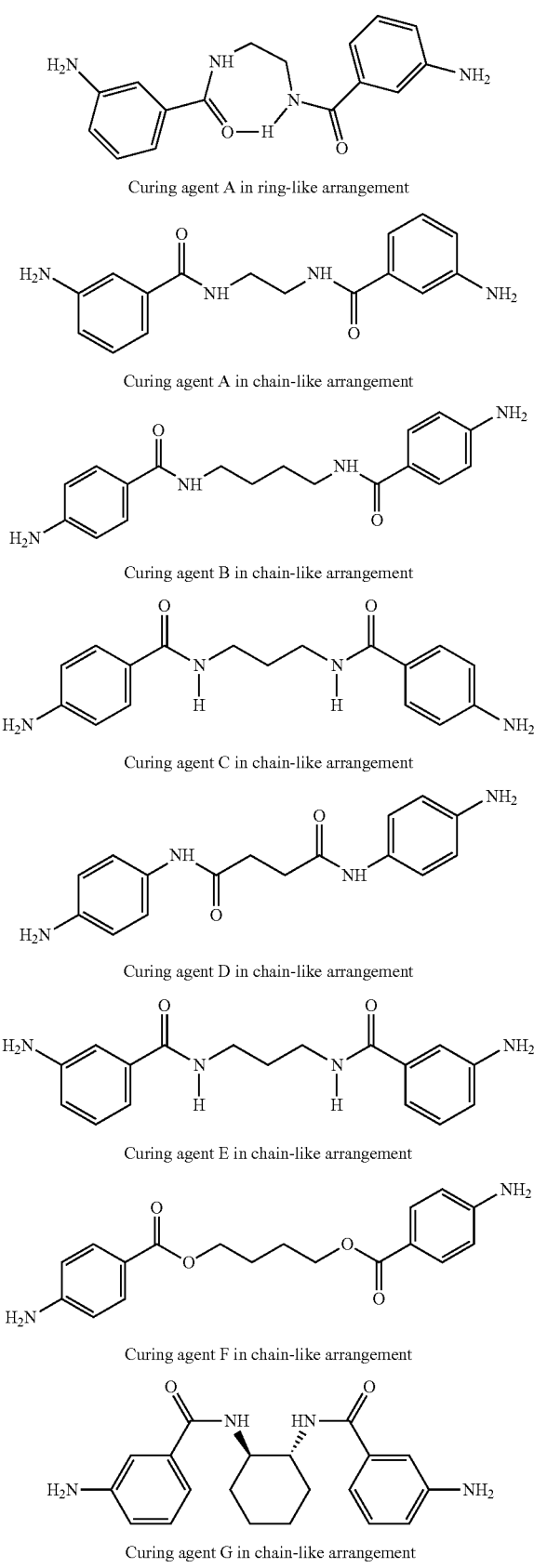

Curing agent A in ring-like arrangement

Curing agent A in chain-like arrangement

Curing agent B in chain-like arrangement

Curing agent C in chain-like arrangement

Curing agent D in chain-like arrangement

Curing agent E in chain-like arrangement

Curing agent F in chain-like arrangement

Curing agent G in chain-like arrangement

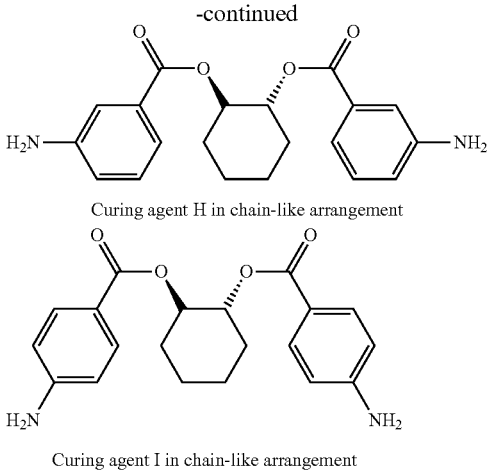

Curing agent H in chain-like arrangement

Curing agent I in chain-like arrangement

Figure 1:
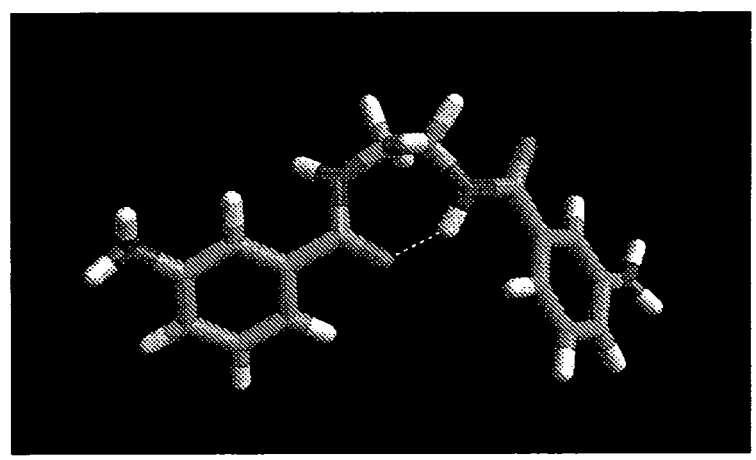

FIG. 1 shows an image of curing agent A generated by the open-source simulation software "Avogadro" using the MM94 force field. The curing agent is in its ring-like arrangement and was shown in the simulation software to be a stable arrangement. The distance between the nitrogens is 12.85 angstroms.

Figure 2:
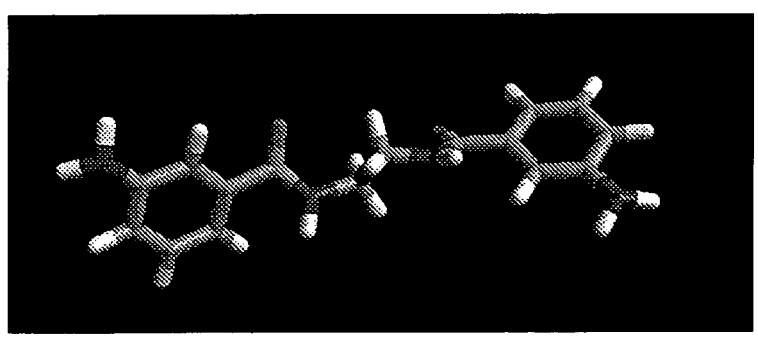

FIG. 2 shows another image of curing agent A generated by the same simulation software. The curing agent is in its chain-like arrangement and was also shown to be a stable arrangement. The distance between the nitrogens is 13.73 angstroms.

Figure 3:
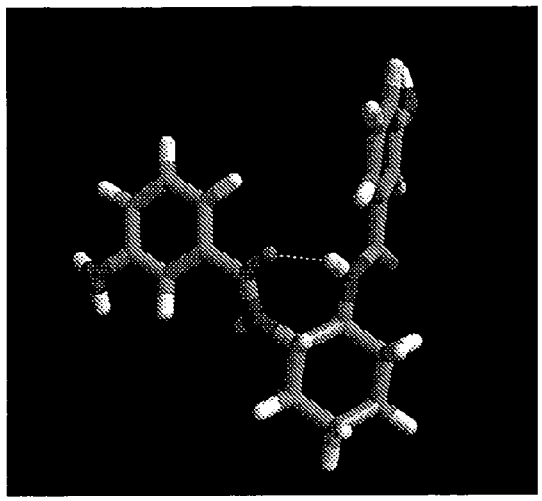

FIG. 3 shows an image of curing agent G generated by the same simulation software. The curing agent is in a first ring-like arrangement, wherein the cyclohexane group is in its chair form, and was also shown to be a stable arrangement. The structure has a potential energy (MMFF94 force field) of 31.05 kJ/mol. The distance between the nitrogens is 7.8 angstroms.

Figure 4:
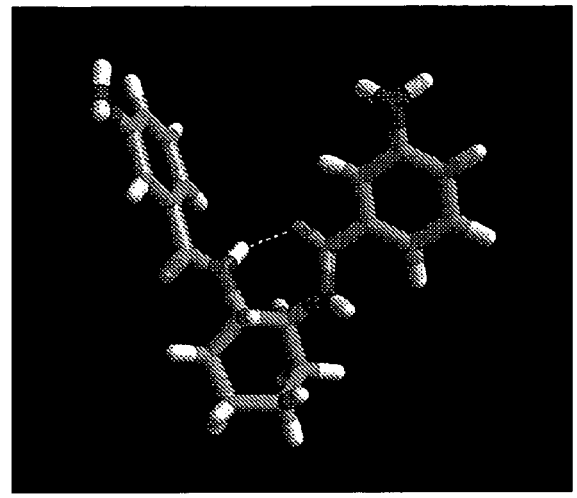
FIG. 4 is an image of the curing agent of FIG. 3 wherein the cyclohexane group is in its boat form.

FIG. 4 shows an image of curing agent G generated by the same simulation software. The curing agent is in a second ring-like arrangement, wherein the cyclohexane group is in its boat form, and has also shown to be a stable arrangement. The structure has a potential energy (MMFF94 force field) of 55.19 kJ/mol. The distance between the nitrogens is 11 angstroms.

Figure 5:
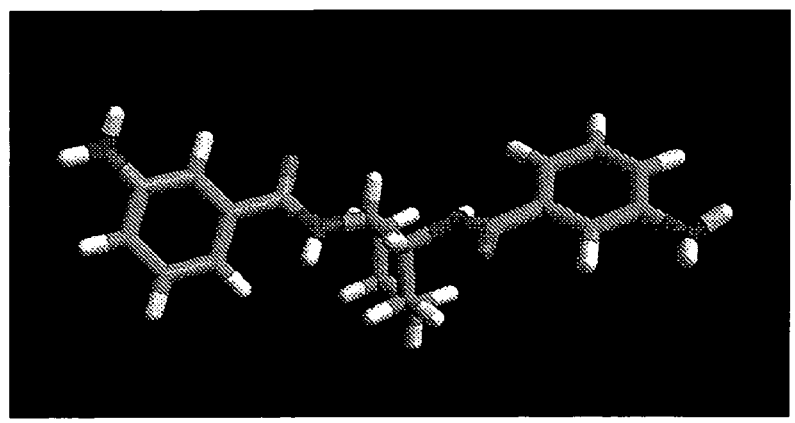
FIG. 5 is an image of the curing agent of FIGS. 3 and 4 in chain-like arrangement.

FIG. 5 shows an image of curing agent G generated by the same simulation software. The curing agent is in its chain-like arrangement, and has also shown to be a stable arrangement. The structure has a potential energy (MMFF94 force field) of 61.4 kJ/mol and the distance between the nitrogens is 16 angstroms.

Preparation of Curing Agent A 100 grams of ground 3-nitrobenzoyl chloride were added at room temperature over 30 minutes to a stirred vessel containing 15.43 g diaminoethane and 27.2 g of triethylamine in 500 ml chlorobenzene. An exotherm to 38° C. was recorded. The temperature was raised to 50° C. for 1 hour. The product was cooled, filtered, washed with acetone and water and dried in vacuo to yield 66 g of a very pale yellow powder (72.5%). 65 g of this dinitro compound was taken and reduced by dispersing in 250 ml of industrial methylated spirit in a 1 liter flask with nitrogen bleed, and adding 3 g of 10% palladium on activated carbon and, drop-wise over 2 hours, 50 ml of hydrazine hydrate. The mixture exothermed to 40° C. and became darker as the nitro compound dissolved. The temperature was then raised to 70° C. where it was held for 90 minutes and then allowed to cool.

The mixture, now containing the desired amino compound A, was filtered and the product retained by the filter was slurried in water and the solid acidified with dilute hydrochloric acid until fully dissolved. This solution was filtered to remove Pd/C and the filtrate neutralised with ammonia solution. A white solid separated which was filtered off and washed with distilled water. The product was dried in vacuo to yield 44 g of powder, 81% of theoretical, melting at 210° C.

Other curing agents were prepared similarly: curing agent B, mp 240° C.; curing agent C, mp 246° C.; curing agent D, mp 140° C.; curing agent E, mp 120° C.

Curing agents B to E were prepared in the same manner as curing agent A. Curing agent F was prepared by transesterification of ethyl 4-aminobenzoate and 1,4-butanediol and is obtained as a white powder, mp 208° C., but could equally well be prepared by a similar method to curing agents A to E, via catalytic hydrogenation of the corresponding nitro compound.

Preparation of Curing Agent G

The dinitro precursor was first prepared. A portion of 28.44 g of trans-1,2-diaminocyclohexane was weighed into a 1000 ml flask together with 26.4 g of triethylamine and 300 g chlorobenzene. With mechanical stirring, powdered 3-nitrobenzoylchloride, 97 g, was added at room temperature over 1 hour and further chlorobenzene added as needed to maintain mobility. The mixture exothermed to 30° C. The mixture was cooled, filtered, and washed with IMS and water. After drying at 80° C. a white powder was obtained, 71 g, 69% yield, melting at 266° C.

The amine was prepared from the above dinitro compound as follows. Into a 1 liter flask were placed 68 g of the dinitro compound, 250 ml IMS and 2.7 g of 10% palladium on carbon (previously wetted with 50 ml IMS). With efficient stirring under nitrogen, 45 ml of hydrazine hydrate was added dropwise over 1 hour and then the temperature was raised to 60° C. for 2 hours. The product was cooled, filtered and washed with IMS and water. The crude solid was worked up by dissolving in warm dilute hydrochloric acid then filtered to remove carbon. The pale yellow filtrate was neutralised with ammonium hydroxide solution and the resulting white solid was filtered, washed with water and dried in vacuo. A white powder was obtained in 90% yield (52.3 g) and melting at 274-276° C.

$^1$H NMR (DMSO-d6): δ 1.24-1.93 (multiplets, 8H, cyclohexane —CH$_2$—); 3.84 (2H, —CH); 5.19 (singlet, 4H, —NH$_2$); 6.65 (m, 2H, 5-H on aromatic ring); 6.85 (m, 2H, 4-H on aromatic ring); 7.0 (m, 4H, aromatic ring); 8.00 (d, 2H amide H?).

Preparation of Curing Agent H

The dinitro precursor was prepared from trans-1,2-cyclohexanediol (20 g) and triethylamine (36.5 g) in chlorobenzene (500 ml) by adding 3-nitrobenzoyl chloride (67.09 g) slowly over 1 hour. The temperature was raised to 50° C. for 2 hours. The product was filtered to remove triethylamine hydrochloride. The filtrate was rotary evaporated yielding a yellow oil which on crystallisation was filtered and washed with IMS giving a white powder, 41 g (58%), melting point 102-104° C.

The amine was made as above from 40 g of the dinitro precursor, 150 ml IMS, 1.53 g Pd on carbon, and 26 ml hydrazine hydrate added over 1.5 hours. Effervescence was vigorous. A maximum exotherm to 25° C. was maintained. The mixture was then heated to 60° C. for 2 hours. A white product began to be deposited after 1 hour and after cooling was filtered off. The solid was extracted into dilute HCl and filtered to remove the Pd/C. The acidic solution was neutralised with ammonia. A white solid was obtained after drying, 27 g (79%), melting at 137-139° C.

$^1$H NMR (DMSO-d6): δ 1.41-2.51 (multiplets, 8H, cyclohexane —CH$_2$—); 5.08 (2H, —CH); 5.34 (singlet, 4H, —NH$_2$); 6.75 (m, 2H, aromatic ring); 7.03 (m, 6H on aromatic ring).

Preparation of Curing Agent I

An attempt was made to prepare this compound by transesterification of the diol with p-aminoethylbenzoate as for the previous ester-amines[1]. No product was isolated and it is assumed that the diol is too sterically hindered or that it is too volatile to react at ambient pressure. It was therefore necessary to employ the usual acid chloride/alcohol esterification reaction.

The dinitro precursor was prepared from trans-1,2-cyclohexanediol (50 g) and triethylamine (91.25 g) in chlorobenzene (500 ml) in a 1 liter flask by adding 4-nitrobenzoyl chloride (167.7 g) slowly over 1 hour with efficient stirring. The temperature exothermed to 50° C. After further heating to 50° C. for 90 minutes the mixture was cooled and filtered to remove triethylamine hydrochloride. The filtrate was rotary evaporated yielding a yellow solid which was washed with IMS and water giving a white powder, which after drying in vacuum weighed 170 g (96%), melting point 124-126° C.

The amine was made as above from 80 g of the dinitro precursor in 300 ml IMS in a 1 liter flask, with 3 g Pd on carbon, and 52 ml hydrazine hydrate added dropwise over 1.5 hours. Effervescence was vigorous. The reaction exothermed to 43° C. The mixture was then heated to 60° C. for 1.5 hours. A white product began to be deposited after 30 minutes, and after cooling was filtered off. The solid was extracted into warm, dilute HCl and filtered to remove the Pd/C. The acidic solution was neutralised with ammonia with grinding. A white powder melting at 175-178° C. was obtained after washing with water and drying, 59.2 g (87%).

$^1$H NMR (DMSO-d6): δ 1.38-2.04 (multiplets, 8H, cyclohexane —CH$_2$—); 4.99 (2H, —CH); 5.94 (singlet, 4H, —NH$_2$); 6.5 (m, 4H, 2-H on aromatic ring); 7.56 (m, 3-H on aromatic ring).

Cured Resin Properties

The curing agents above were tested for their reaction with epoxy resins. The following mixtures were prepared and cured at 180° C. for 2 hours. Testing was carried out on a TA Instruments DMA by heating from 25° C. to 250° C. at 5° C./minute and using a frequency of 1 Hz.

All formulations are at a constant epoxy equivalent weight (EW): amine EW of unity to enable a comparison to be made between different systems, and the ratios are based on the theoretical epoxy equivalent weight and amine equivalent weight values.

| Curing agent, gram | Epoxy Resin | | | | Cured Specimen Tg, ° C. |
|---|---|---|---|---|---|
| | MY0600, g | DER 332, g | Rutapox 0158, g | MY721, g | |
| C, 4.0 | 4.74 | 0 | 0 | 0 | 166 |
| B, 5.0 | 0 | 10.4 | 0 | 0 | 156 |
| E, 5.0 | 5.92 | 0 | 0 | 0 | 185 |
| A, 5.0 | 6.2 | 0 | 0 | 0 | 166 |
| A, 3.72 | 4.0 | 0 | 1.0 | 0 | 174 |
| A, 7.45 | 0 | 0 | 0 | 10.5 | 206 |
| A, 6.6 | 0 | 0 | 2.0 | 8.0 | 193 |
| A, 3.72 | 0 | 8.51 | 0 | 0 | 155 |
| F, 6.0 | 6.76 | 0 | 0 | 0 | 144 |
| F, 6.56 | 0 | 0 | 0 | 8.44 | 197 |
| G, 3.52 | 0 | 0 | 0 | 2.11* | 181 |
| H, 4.42 | 0 | 0 | 0 | 5.28 | 207 |

| Curing agent, gram | Epoxy Resin | | | | Cured Specimen Tg, °C. |
|---|---|---|---|---|---|
| | MY0600, g | DER 332, g | Rutapox 0158, g | MY721, g | |
| H, 4.42 | 4.62 | 0 | 0 | 0 | 167 |
| I, 4.42 | 0 | 0 | 0 | 5.28 | 206 |
| I, 4.42 | 4.62 | 0 | 0 | 0 | 191 |

The table shows the proportions of various resins used and the Tg of the cured specimens. Tg is recorded as the onset of the drop in the storage modulus.
*The MY721 was blended in this case with 2.84 g of diglycidyl-1,2-cyclohexanecarboxylate.

The resulting cured resins had a flexible nature whilst useful Tgs are obtained.

Araldite MY0600 is a triglycidyl epoxy resin derived from 3-aminophenol and MY 721 is a tetraglycidyl derivative of 4,4'-diaminodphenylmethane. Both are supplied by Huntsman. DER 332 is a diglycidyl ether of bisphenol A supplied by Dow. Riitapox 0158 is a diglycidyl ether of bisphenol F supplied by Hexion.

The curable resins used have the following structures:

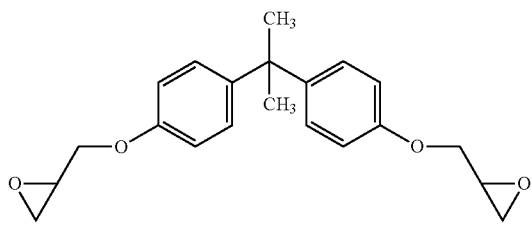

Diglycidyl ether of Bisphenol A (e.g. DER 332)

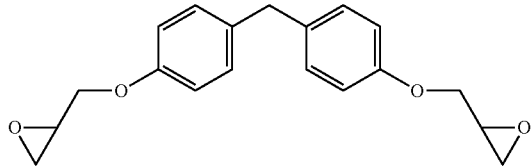

Diglycidyl ether of Bisphenol F (e.g. Rutapox 0158)

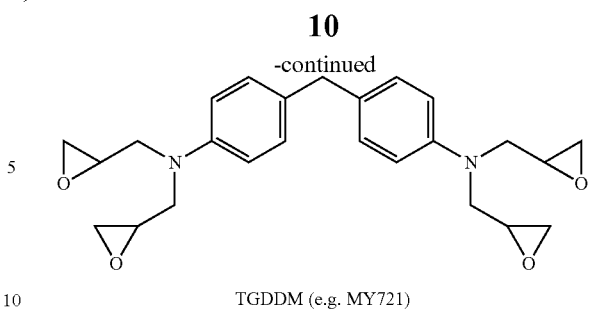

TGDDM (e.g. MY721)

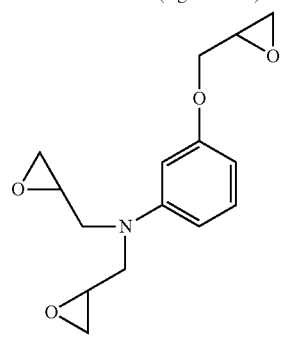

Triglycidyl derivative of m-aminophenol (e.g. MY0600)

The invention claimed is:

1. A curable resin comprising a curable epoxy resin which comprises a triglycidyl derivative of m-aminophenol and a curing agent for said curable epoxy resin, wherein the curing agent is adjustable between a chain-like arrangement and a ring-like arrangement in response to tensile stress, shear stress, impact stress or flexure stress wherein said curing, agent has the formula X1-B—X2 wherein each of X1 and X2 is a benzene ring with a single —NH, functional reactive group located at the para position with respect to the B-sequence and wherein B consists of two —CO—O— structures located on adjacent carbons of cyclohexane.

2. A cured resin obtained by curing a curable resin that comprises a curable resin which comprises a triglycidyl derivative of m-aminophenol and a curing, agent for said curable resin wherein said curing agent has the formula X1-B—X2 wherein each of X1 and X2 is a benzene ring with a single functional reactive group located at the para position with respect to the B-sequence and wherein B consists of two —CO—O— structures located on adjacent carbons of cyclohexane.

* * * * *